(12) United States Patent
Hsieh et al.

(10) Patent No.: US 9,797,838 B2
(45) Date of Patent: Oct. 24, 2017

(54) SCREENING METHOD FOR RAPID IDENTIFICATION OF HYBRIDOMAS

(71) Applicant: Tunghai University, Taichung (TW)

(72) Inventors: Chang-Chi Hsieh, Taichung (TW); Ming-Shiou Jan, Taichung (TW); Ai Shih, Tainan (TW); Chuan-Kai Chou, Taipei (TW); Yen-Wan Hsiao, Taichung (TW); Ying-Chun Lai, Taichung (TW)

(73) Assignee: TUNGHAI UNIVERSITY, Taichung (TW)

( * ) Notice: Subject to any disclaimer, the term of this patent is extended or adjusted under 35 U.S.C. 154(b) by 89 days.

(21) Appl. No.: 15/061,525

(22) Filed: Mar. 4, 2016

(65) Prior Publication Data
US 2016/0258957 A1    Sep. 8, 2016

(30) Foreign Application Priority Data
Mar. 6, 2015    (TW) .............................. 104107280 A

(51) Int. Cl.
| G01N 21/64 | (2006.01) |
| G01N 33/569 | (2006.01) |
| G01N 33/577 | (2006.01) |
| G01N 15/10 | (2006.01) |
| G01N 15/14 | (2006.01) |

(52) U.S. Cl.
CPC ...... *G01N 21/6428* (2013.01); *G01N 21/6458* (2013.01); *G01N 33/56966* (2013.01); *G01N 33/577* (2013.01); *G01N 15/1459* (2013.01); *G01N 2015/1006* (2013.01); *G01N 2015/149* (2013.01)

(58) Field of Classification Search
None
See application file for complete search history.

(56) References Cited

U.S. PATENT DOCUMENTS

| 2009/0170773 A1* | 7/2009 | Higashi | C07K 16/28 514/1.1 |
| 2011/0300068 A1* | 12/2011 | Watanabe | C07K 16/22 424/1.49 |
| 2012/0045773 A1* | 2/2012 | Morishita | A61K 31/7088 435/7.1 |

* cited by examiner

*Primary Examiner* — Jacob Cheu
(74) *Attorney, Agent, or Firm* — Ming Chow; Sinorica, LLC

(57) ABSTRACT

This present invention relates to a screening method for rapidly identifying the hybridomas upon cell size and the expression of an exogenous label such as fluorescence labeling. This method of this present invention can largely shortens the time cost for antibody development by saving the time period with comparison of traditional methods using cell culture with media such as HAT medium.

10 Claims, 4 Drawing Sheets

SCREENING METHOD FOR RAPID IDENTIFICATION OF HYBRIDOMAS

The current application claims a foreign priority to application number 104107280 filed on Mar. 6, 2015 in Taiwan.

FIELD OF THE INVENTION

This invention relates to development of monoclonal antibody, more particularly, to a screening method for rapid identification of hybridomas

DESCRIPT OF PRIOR ART

The literature published in 1975 had disclosed the application of hybridomas, hybrid cell lines, in preparation of monoclonal antibody. The prior technology for producing monoclonal antibody was achieved by immunizing the animals through multiple injections with the specific antigens. After immunization, the hybrid cell was generated by fusing a splenocyte of the immunized animal with a myeloma cell within the fusion medium containing polyethylene glycol (PEG). The objective hybrid cell was successfully selected upon the characteristics of splenocyte and myeloma cell including ex vivo viability and DNA synthesis with the selection medium such as HAT medium (hypoxanthine-aminopterin-thymidine medium). Then, the selected hybrid cell was further monoclonalized to produce monoclonal antibody. Finally, the specificity of the monoclonal antibody was determined by ELISA.

Generally, it took at least one month for generation of antibody-producing cells by immunization on the animal. Then, it took about 1 day to generate hybridomas by cell fusion, and several weeks to identify the hybridoma using HAT medium. Finally, it took one month for the monoclonalization of hybridomas and the determination of antibody specificity, respectively. As is described above, development of the monoclonal antibody had to spend about 3~6 months, so it becomes the limitation in the industry of antibody development. Due to the growing requirement in monoclonal antibodies and coveted market of these newly derived antibodies, the traditional methods limit us in rapidly developing the efficient antibodies. Although some technological breakthroughs had been developed in antigen design and immunization to shorten the time cost in inducing immunization, however, the approach to shorten the time period in identifying the hybridoma that produce specific monoclonal antibody is still lacked. Even though the robotic high throughput screening is developed by some large caps, however, this method can't be widely adopted by all antibody development companies with different capital scales due to the huge cost.

Therefore, the shortcomings such as long preparation time period and exorbitant cost are still existed in the field of monoclonal antibodies development. Therefore, development of the screening method to rapidly identify the monoclonal antibody against specific antigen is the critical issue in biomedicine industry.

SUMMARY OF THE INVENTION

The major object of the present invention is to provide a screening method for rapid identification of hybridomas, wherein it can rapid identify the hybridoma by analyzing the expression of an exogenous label and cell size.

Another object of the present invention is to provide the screening method for rapid identification of hybridomas, wherein it largely shortens the time cost for developing monoclonal antibodies without cell culture using selection media.

Still another object of the present invention is to provide the screening method for rapid identification of hybridomas, wherein it is quite simple to avoid technological difficulty and cost in development of monoclonal antibodies. Therefore, the present method is suitable for antibody development companies with various capital scales.

In order to achieve these foresaid purposes, the present invention discloses the a screening method for rapid identification of hybridomas including fusing an immunized splenocyte and a myeloma cell, and selecting a hybridoma by analyzing the expression of an exogenous label and cell size in a cell, wherein the characteristics of the hybridoma including expressing the exogenous label and having larger size than the splenocyte and the myeloma cell.

Preferably, the exogenous label is a fluorescence label.

Preferably, the hybridoma is with the fluorescence label because of the splenocyte with the fluorescence label, wherein the fluorescence labeled splenocyte is prepared from a non-human transgenic animal carrying a fluorescence gene or is treated by immunofluorescence staining before cell fusion.

Preferably, the hybridoma is with the fluorescence label because of the myeloma cell with the fluorescence label, wherein the myeloma cell can express a gene encoding a fluorescence protein or the myeloma cell is treated by immunofluorescence staining before cell fusion.

Preferably, it is using the flow cytometry analysis or/and fluorescent microscopy to analyze the cell.

DETAILED DESCRIPTION OF THE INVENTION

Figure 1:
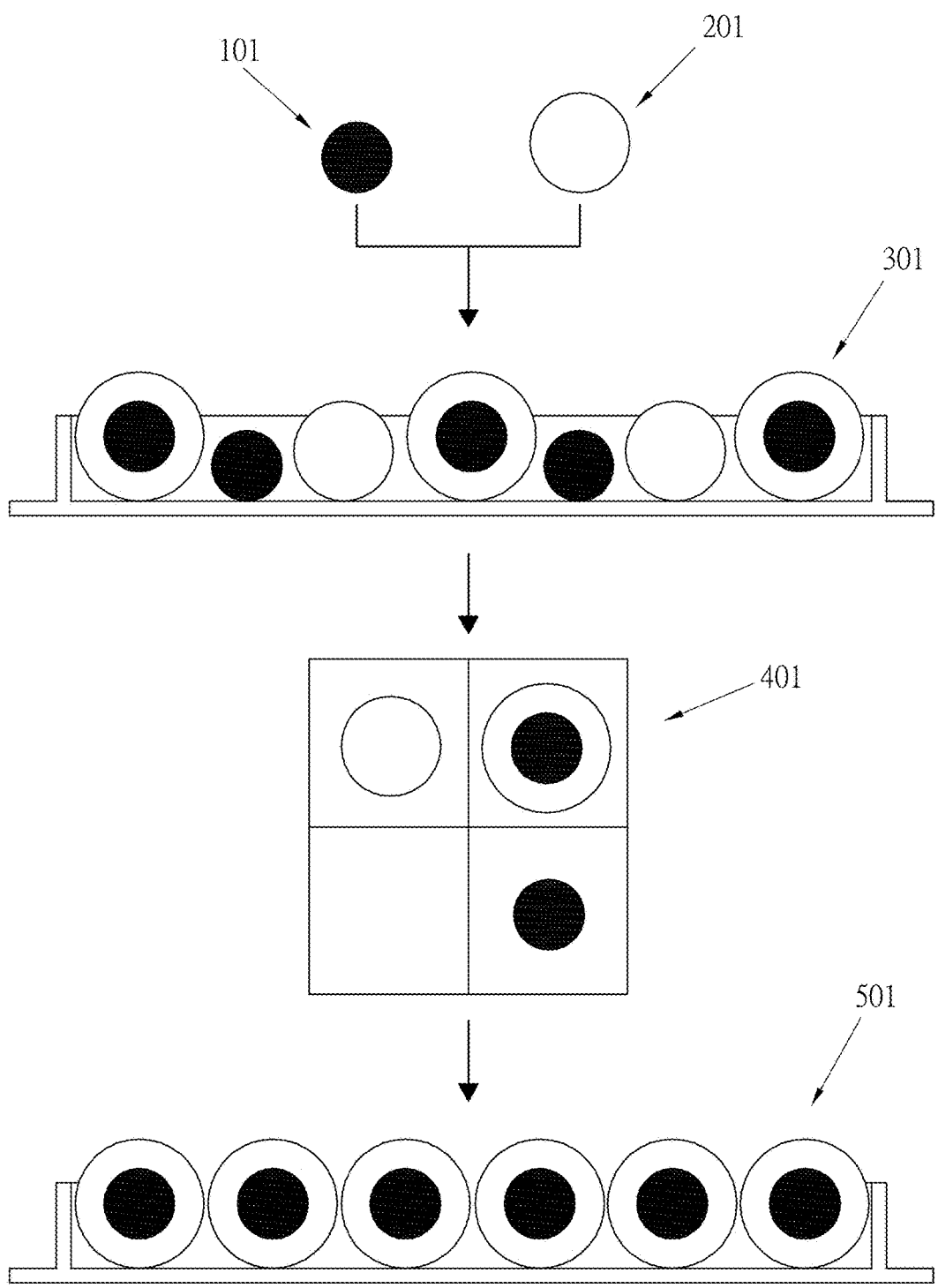
FIG. 1 shows the flow chart of the embodiment of the present invention.

The present invention discloses a screening method for rapid identification of hybridomas through analyzing a cell whether expresses an exogenous label, such as fluorescence, and the size of the cell. According to the method of the present invention, the hybridoma can be successfully identified with shortened time period compared to the previous method using cell culture with HAT medium. It efficiently shortens the time cost for developing monoclonal antibodies.

The technical term or the scientific term that will be used in the specification has the same meaning as a person skilled in the art commonly understood unless defined differently.

The term "hybridoma", "hybrid cell line" or "hybrid cell" refers to a cell or a cell line that is produced by fusing at least two different cells to one cell. In the present invention, the two different cells are an antigen-immunized splenocyte and a myeloma cell, respectively.

The term "cell fusion method" or "fusion" or "fusing" refers to a method in which two or more cells are combined to form a single hybrid cell which contains all or part of at least the nucleic acid content of each individual cell. Fusion may be accomplished by any method of combining cells under fuseogenic conditions well known in the art. For example, PEG is the most widely used chemical reagent to trigger cell fusion during development of monoclonal antibodies. The cell fusion can be also achieved by the physical method using electric pulse. In addition, the biological method for cell fusion is induced by the inactivated virus.

The term "antigen-immunized splenocyte" refers to the antibody producing-splenocyte, -B lymphocyte, or -B cell. Generally, the splenocyte is able to secrete the specific antibody by injecting the antigen into the animal to induce splenocyte maturation. At this time, the splenocyte could be directly obtained from immunized animal or be prepared through in vitro immunization of normal splenocytes by antigen during culture.

The term "tumor cell" is also known as "cancer cell" that bears immortality in cultured medium. Recently, the myeloma cell is the most widely used cancer cell line for preparation of monoclonal antibody. For example, the myeloma cell lines including NS-1 cell, SP2/0 cell, and P3X63Ag8.U1 cells are cancer cell lines derived from BALB/c mice. In addition, the myeloma cell lines including RPMI8226 cell, MC/CAR cell, IM-9 cell, UC 729-6 cell, and LTR228 cell are human cancer cell lines.

The term "fluorescent gene" refers to the gene encoding protein with different excitation wavelengths in the cell. For example, the green fluorescent protein bears excitation peak at a wavelength of 508 nm.

The term "transgenic animal" refers to the animals carrying an exogenous transgene in the genome. The exogenous transgene is usually introduced into embryonic stem cell or fertilized egg via genetic engineering technology. In addition, the exogenous transgene is expressed in the destined cells through the genetic engineering to construct the specific promoter and the exogenous gene on the vector.

In the following, there are several embodiments with figures for further describing and illustrating the present invention.

According to FIG. 1, the first embodiment of the present invention discloses a screening method for identifying hybridomas 10 including the following steps:

Step 101: Providing an antigen-immunized splenocyte from a splenocyte is derived from a BALB/c GFP transgenic mouse that is immunized by specific antigen to induce antibody production.

Step 201: Providing a NS-1 myeloma cell.

Step 301: Fusing the splenocyte with the NS-1 myeloma cell by treatment of PEG.

Step 401: Analyzing the cell size and fluorescence intensity of the cells from step 301 by flow cytometry analysis.

Step 501: Isolating a hybrid cell which is larger than the splenocyte and the NS-1 myeloma cell cell size and expresses the green fluorescent protein by cell sorting.

According to the above-mentioned method, the hybrid cell can be selected from the splenocyte and the myeloma cell. Furthermore, the hybrid cell is selected from the myeloma cells upon the expression of green fluorescent protein by flow cytometry. In addition, it can be also selected from the splenocyte upon its larger cell size by flow cytometry. Therefore, by the method of the present invention, it spends only 1 to 2 days to rapidly identify the hybrid cell.

It depends on the cell size and the fluorescence intensity to select the hybrid cell. The origin of the fluorescence in the hybrid cell could be obtained from either the splenocyte or the myeloma cell.

In the second embodiment of the present invention provides a screening method for identifying hybridomas comprising the similar steps with comparison of the first embodiment. The difference between the first and second embodiment is the origin of fluorescence, wherein the splenocyte of the normal mice is fused with NS-1 cell, that is introduced with the transgene encoding green fluorescent protein. Accordingly, the objects of the present invention can be also achieved.

Furthermore, the myeloma cell expresses the gene encoding the fluorescent protein through fluorescence labeling or genetic engineering.

In addition, the person skilled in the art would clearly understand that such method, instrument, kit, platform can be applied to analyze the fluorescence intensity and cell size. For example, the instrument is fluorescence microscopy. Accordingly, the present invention discloses a method to identify the hybridomas with only 1 to 2 days that is quite faster than the traditional method using selection media such as HAT medium for couple weeks. Therefore, the preset invention enables us largely shorten the time period and cost for preparing monoclonal antibodies.

The following example with figures are to further demonstrate the present invention.

EXAMPLE

Cell Fusion

The NS-1 cells transfected with GFP gene were cultured before the cell fusion. On the day before cell fusion, passage of NS-1 cells was performed and was followed by cell culture until the growing cells occupy 50%-60% capacity of culture dish. The cultured cells were collected for centrifugation at 1000 rpm. Then, the supernatant was discarded for re-suspending the cell palate and cell counting.

Prefusion boosting was performed on the immunized mice on 3 days before cell fusion. On the day of cell fusion, spleen was collected from the mouse anesthetized by isoflurane. The collected spleen in 200-mesh steel cell strainer, that was placed in 6-cm dish containing 5 ml serum free DMEM, was homogenized to release the splenocytes. The 5 ml splenocyte-containing suspension was then filtered the 70-um cell strainer put on 5 ml centrifuge tube. The 70-um cell strainer was further washed by 10 ml serum free DMEM. 15 ml collected medium was collected for centrifugation at 1000 rpm for 5 minutes to spin down the splenocytes. After discarding the supernatant, 5 ml RBC (Red Blood Cells) lysis buffer was added and was incubated for 5 minutes to lyse the red blood cells. After the incubation, 35 ml serum free DMEM was added to dilute RBC lysis buffer and was centrifuged at 1000 rpm for 5 minutes. After discarding the supernatant, 20 ml serum free DMEM was added to re-suspend the cell plate for cell counting.

NS-1 cells and splenocytes were mixed well in a ratio about 1:1 to 1:5, first. Then, 1~2 ml cell fusion buffer (serum free DMEM with 50% PEG-4000) was added. In the next step, 1~2 ml serum free DMEM was added to be mixed well with cell fusion buffer. Finally, 7 ml serum free DMEM was added and was followed by centrifugation at 1000 rpm for 5 minutes. After discarding the supernatant, the cell plate was re-suspended by 10 ml serum free DMEM and was cultured in cell incubator.

Calculating the number of the hybrid cells were prepared from cell fusion reaction. In addition, some of the hybrid cells were aliquoted as the control group. The others were placed in the centrifuge tube for centrifugation at 1000 rpm for 5 minutes to spin down the hybrid cells. After discarding the supernatant, 1 ml DMEM-20 (20% FBS, 1 mM Sodium pyruvate, 10 mM HEPES, 10 ug/ml gentamicin) was added to re-suspended the cell palate and was further centrifuged at 1000 rpm for 5 minutes. After discarding supernatant, 1 ml staining buffer (PBS, 3% FBS, 0.22 um filtered) was added to re-suspend the cell palate for cell counting. Finally, the hybrid cells with green fluorescence were isolated by cell sorter.

Figure 2:
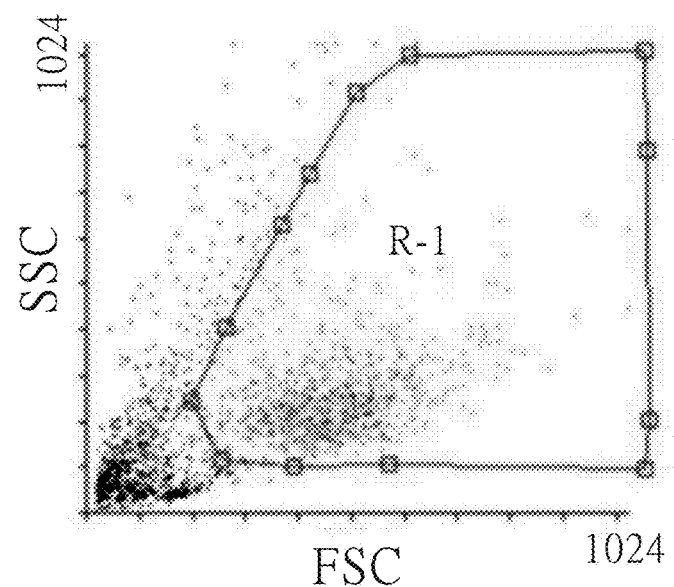
FIG. 2 shows the dot plots of FSC versus SSC with R-1 region by Flow cytometry.
Figure 3:
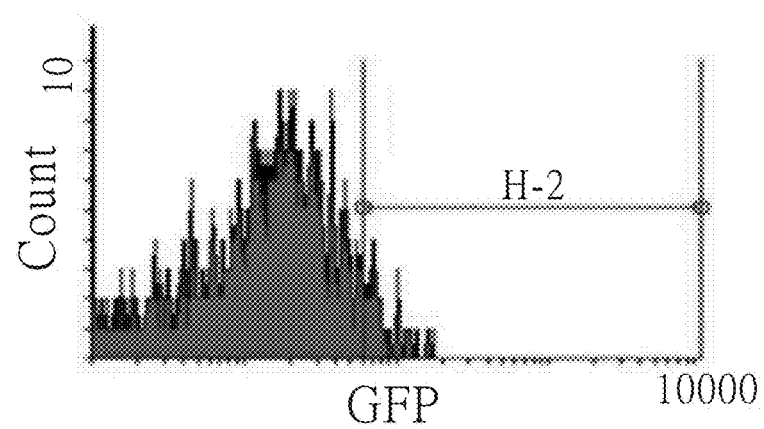
FIG. 3 shows the result for counting the cells of R-1 region.
Figure 4:
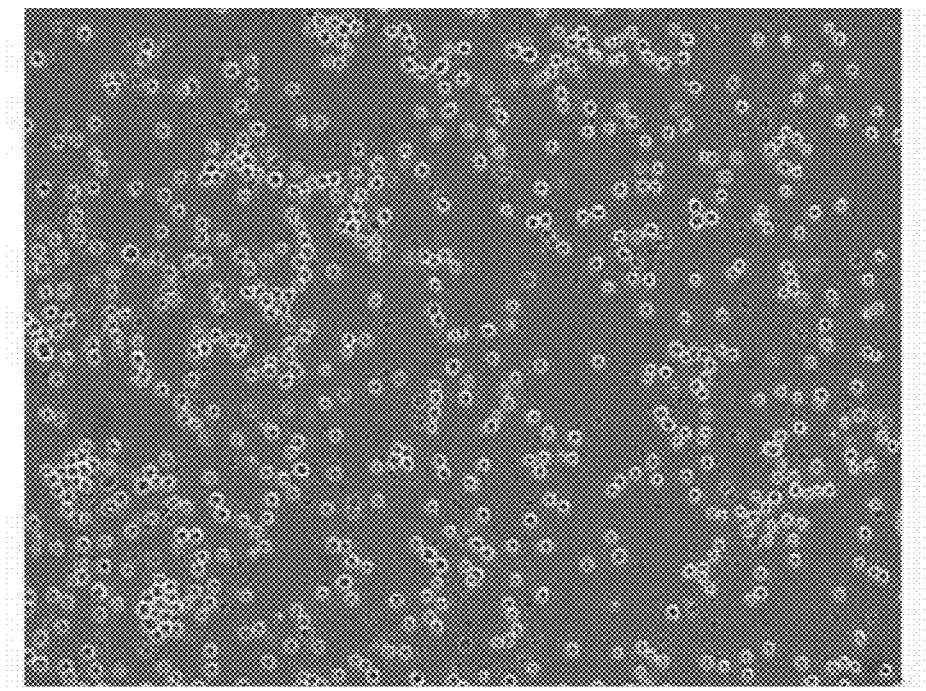
FIG. 4 shows the result of observing the cultured cells by microscopy.
Figure 5:
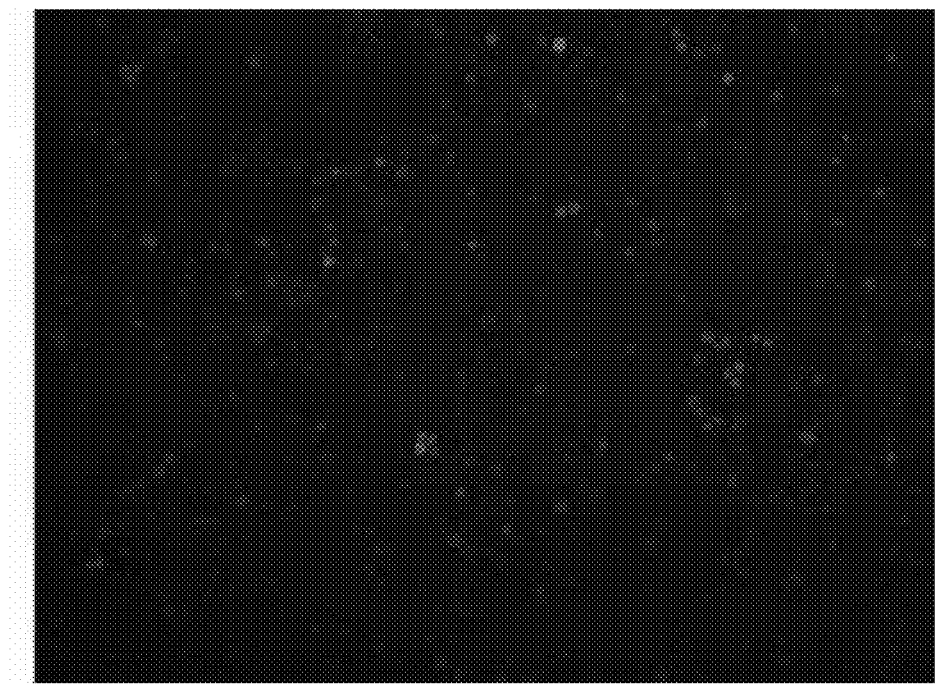
FIG. 5 shows the result of observing the cultured cells by fluorescent microscopy.
Figure 6:
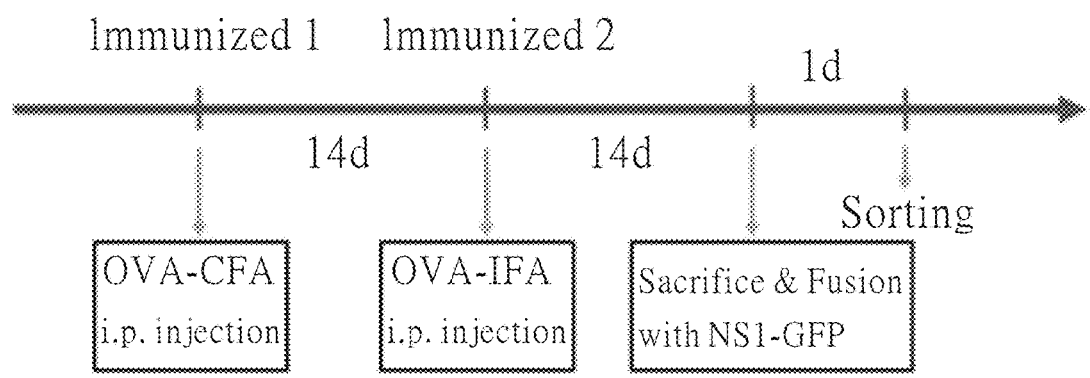
FIG. 6 shows the time schedule of the present invention.

Please see the FIGS. 2 to 5, it shown that the cell area is R-1 in the FIG. 2 and about 14.7% of the cells express the enhanced fluorescence intensity of GFP. According to the result, it suggested that method of the present invention can select the fusion cell fused by the NS-1 cell expressing GFP and the splenocyte from the normal mice. Moreover, as shown in FIG. 6, it suggested that the method of the present invention is able to efficiently shorten the time cost for preparing monoclonal antibodies.

The above-mentioned detailed description and specific examples are only for illustrating of this present invention. Any easy change or modification based on examples in the description by the person skilled in the art of this present invention will be included within the scope of following claims.

What is claimed is:

1. A screening method for rapid identification of hybridomas includes the following steps:
    (a) fusing an antigen-immunized splenocyte and a myeloma cell by cell fusion, wherein either the antigen-immunized splenocyte or the myeloma cell is transfected with exogenous label gene before cell fusion;
    (b) selecting a hybridoma by identifying larger size cell than splentocyte and myeloma cell and the expression of said exogenous label on the cell.

2. The screening method for rapid identification of hybridomas to claim 1, wherein the exogenous label is fluorescence label.

3. The screening method for rapid identification of hybridomas to claim 2, wherein the splenocyte is labeled by fluorescence.

4. The screening method for rapid identification of hybridomas to claim 3, wherein the splenocyte is derived from a non-human transgenic animal carrying a transgene encoding fluorescent protein.

5. The screening method for rapid identification of hybridomas to claim 3, wherein the splenocyte is labeled through staining with the antibody conjugated with fluorescence.

6. The screening method for rapid identification of hybridomas to claim 2, wherein the myeloma cell is labeled by fluorescence.

7. The screening method for rapid identification of hybridomas to claim 6, wherein the myeloma cell carries an exogenous gene encoding fluorescent protein.

8. The screening method for rapid identification of hybridomas to claim 6, wherein the myeloma cell is labeled by staining with the antibody conjugated with fluorescence.

9. The screening method for rapid identification of hybridomas to claim 1, wherein the cell is analyzed by flow cytometry.

10. The screening method for rapid identification of hybridomas to claim 2, wherein the cell is analyzed by fluorescent microscopy.

* * * * *